US010486125B2

United States Patent
Scotto et al.

(10) Patent No.: US 10,486,125 B2
(45) Date of Patent: Nov. 26, 2019

(54) UREA FINISHING PROCESS WITH ACID SCRUBBING

(71) Applicant: Casale SA, Lugano (CH)

(72) Inventors: Andrea Scotto, Breganzona (CH); Paolo Bertini, Lugano (CH)

(73) Assignee: Casale SA, Lugano (CH)

( * ) Notice: Subject to any disclaimer, the term of this patent is extended or adjusted under 35 U.S.C. 154(b) by 389 days.

(21) Appl. No.: 15/526,190

(22) PCT Filed: Aug. 13, 2015

(86) PCT No.: PCT/EP2015/069857
§ 371 (c)(1),
(2) Date: May 11, 2017

(87) PCT Pub. No.: WO2016/074813
PCT Pub. Date: May 19, 2016

(65) Prior Publication Data
US 2017/0312717 A1 Nov. 2, 2017

(30) Foreign Application Priority Data
Nov. 12, 2014 (EP) ..................................... 14192905

(51) Int. Cl.
*B01J 2/00* (2006.01)
*C07C 273/16* (2006.01)
(52) U.S. Cl.
CPC ............. *B01J 2/003* (2013.01); *C07C 273/16* (2013.01)
(58) Field of Classification Search
CPC ............................... B01J 2/003; C07C 273/16
See application file for complete search history.

(56) References Cited

FOREIGN PATENT DOCUMENTS

| JP | 2000 001466 A | 1/2000 |
|---|---|---|
| JP | 2000001466 A * | 1/2000 |

(Continued)

OTHER PUBLICATIONS

Machine translation of JP-2000001466-A accessed Jul. 22, 2019 (Year: 2019).*

(Continued)

*Primary Examiner* — Cabrena Holecek
(74) *Attorney, Agent, or Firm* — Akerman LLP

(57) ABSTRACT

A process for the finishing of urea comprising: (a) removing water from an aqueous urea solution in a first evaporation and condensation section, obtaining a urea melt; (b) subjecting said urea melt to a finishing treatment comprising granulation and resulting in solid urea and air contaminated with urea dust and ammonia; (c) subjecting said contaminated air to acid scrubbing, producing an aqueous solution comprising urea and ammonium salts; (d) subjecting at least part of said aqueous solution to evaporation in a second evaporation section, obtaining a liquid stream comprising urea and ammonium salts and a gaseous stream; (e) condensing said gaseous stream in a second condensation section, obtaining a recycle aqueous stream; (f) using at least a part of said recycle aqueous stream for the scrubbing of contaminated air; (g) converting at least a portion of said liquid stream comprising urea and ammonium salts into solid particles, and (h) using said solid particles as seeds for the granulation; a corresponding urea plant and method of revamping a urea plant are also disclosed.

16 Claims, 6 Drawing Sheets

(56) References Cited

FOREIGN PATENT DOCUMENTS

WO    02/083320  A1    10/2002
WO    2011/032786 A1    3/2011

OTHER PUBLICATIONS

International Search Report issued in connection with PCT/EP2015/069857.
Meessen, "Urea" in "Ullmann's Encyclopedia of Industrial Chemistry", 2012, Wiley-VCH Verlag, vol. 37, pp. 657-695.

* cited by examiner

UREA FINISHING PROCESS WITH ACID SCRUBBING

This application is a national phase of PCT/EP2015/069857, filed Aug. 31, 2015, and claims priority to EP 14192905.9, filed Nov. 12, 2014, the entire contents of both of which are hereby incorporated by reference.

FIELD OF INVENTION

The invention relates to a process for the finishing of urea. More in detail, the invention relates to a process involving acid scrubbing of the ammonia-laden air drawn off a granulator or a prilling tower.

PRIOR ART

The production of commercial solid urea comprises the synthesis of a urea melt and a finishing step of conversion of said melt in a solid form. Techniques for said conversion include for example the prilling process and the granulation process.

The known techniques for synthesis and finishing of urea are described in the literature, for example in the Ullmann's Encyclopedia of Industrial Chemistry, Wiley-VCH Verlag, vol. A27. In general terms, an aqueous solution comprising urea is formed in a synthesis section and optionally in a recovery section; said solution, having a urea content generally around 60-80% in weight, is sent to an evaporation and condensation section to produce said urea melt.

The granulation process is carried out in a granulation unit, usually in a fluidized bed state. Fluid-bed granulators are known in the art; a process for granulation and a related fluid-bed granulator are disclosed for example in WO 02/083320.

The granulation process requires an air flow for keeping the fluidized-bed state of granules and/or for cooling. This air comes into direct contact with the urea melt and with the solid urea particles, resulting in a contamination of air with some urea dust and ammonia. Similarly, a prilling tower releases a flow of contaminated cooling air.

Hence, a problem of granulators and prilling towers is that they release a contaminated air flow including ammonia and a small but non-negligible amount of urea. Said flow must be treated to remove contaminants, in particular to remove the ammonia, and to recover the urea.

It is known that ammonia can be removed by acid scrubbing, for example by scrubbing the ammonia-containing air flow with an acid solution, for example a solution of sulphuric acid. Acid scrubbing produces an ammonium salt solution containing urea and small amounts of ammonium salts, for example ammonium sulphate. Said solution can be evaporated to recover urea and vapors obtained can be condensed to recover water. However, sending said ammonium salt solution to the above mentioned evaporation and condensation section, which converts the urea solution into urea melt, has the disadvantage to contaminate the water released by said section with ammonium salts. Said water recovered from the main condensation section is normally sent to a water treatment section which is designed to remove ammonia and urea but is generally unable to remove ammonium salts. Hence, contamination with ammonium salts is detrimental to said treatment section. In addition, the water recovered from said treatment section is normally used as a boiler feed water (BFW) for heat recovery and production of steam, and ammonium salts in the water may damage the tubes of shell-and-tube heat recovery boilers with a considerable risk of failure.

The finishing section poses problems also when an existing urea plant is revamped, especially because an existing granulator or prilling tower may be unable to cope with an increased capacity, thus being a bottleneck of the plant. For example, prilling towers are large and expensive equipment and adding capacity to a prilling tower is often not feasible or too expensive.

SUMMARY OF THE INVENTION

The purpose of the invention is to avoid the above drawbacks of the prior art.

Said purpose is achieved with a process for the finishing of urea, an apparatus for the finishing of urea and a method of revamping a urea plant according to the claims.

According to the finishing process of the invention, an aqueous urea solution formed in a urea synthesis plant is subjected to evaporation and condensation in a first evaporation and condensation section to obtain a urea melt.

Said urea melt is at least partially subjected to a finishing treatment resulting in solid urea and a stream of contaminated air containing urea dust and ammonia. Said finishing treatment comprises a step of granulation which is carried out in a granulation unit. In some embodiments of the process, said step of granulation is carried out after a prilling process in a prilling tower. Accordingly, granulation may serve the purpose of fattening urea prills previously formed in a prilling tower. The contaminated air in this case may come from both steps of prilling and granulation.

Said contaminated air is subjected to a scrubbing treatment including an acid scrubbing and a dust scrubbing. Said acid scrubbing is carried out in the presence of an acid which is preferably selected among sulphuric acid, nitric acid and phosphoric acid, or another suitable acid.

Dust scrubbing and acid scrubbing may be carried out in the same environment or separately, according to different embodiments of the invention.

Said scrubbing treatment produces an aqueous solution containing urea and ammonium salts, for example ammonium sulphate. Said solution is subjected to an additional evaporation in a second evaporation section to separate a liquid stream containing urea and ammonium salts (hereinafter: urea-containing stream), and a gaseous stream comprising water vapor and small amounts of urea and ammonium salts. Preferably said aqueous solution containing urea and ammonium salts is directly subjected to said additional evaporation, that is without intermediate processing of said solution.

The above mentioned urea-containing stream from the second evaporation section, or at least a portion of it, is used to generate generates solid particles containing urea and ammonium salts. This may be carried out in specific equipment called seeding unit or seeder, installed upstream the granulation unit, or in the prilling tower when provided. Said solid particles are then sent to the granulation unit for their enlargement or fattening. Said solid particles are also termed seeds due to their contribution to the granulation process.

Accordingly, the invention provides that a process of granulation is used to convert a liquid urea into solid granules, with the help of small solid particles acting as seeds of the granulation process. Said solid particles are produced in a seeding unit or in a prilling tower upstream the granulator, using the liquid stream containing urea and ammonium salts which is recovered from the second evaporation section.

The gaseous stream from the second evaporation section is instead subjected to condensation in a second condensation section, which produces an acid aqueous stream which is recycled back to the scrubbing treatment, thus reducing consumption of fresh water.

Some preferred embodiments of the process of the invention are discussed hereinbelow in a greater detail.

In a first embodiment, said at least part of urea melt is directly subjected to granulation. A stream of dust- and ammonia-laden air is drawn off the granulation unit and subjected to the aforementioned scrubbing treatment.

The liquid urea-containing stream from the second evaporation section is used to generate solid particles (seeds) in a seeding unit, and the solid particles are then sent to the granulation unit.

In a second embodiment, a portion of said urea-containing stream from the second evaporation section is sent to the seeding unit, and a remaining portion is sent directly to the granulation unit. This embodiment may be appropriate when the amount of said urea-containing stream exceeds the amount required by the seeding unit.

In a third embodiment, the full amount of the urea-containing stream from the second evaporation section is sent to said seeding unit, together with a minor portion of the urea melt from the first evaporation and condensation section. This embodiment is advantageous if the urea contained in the stream from the second evaporation section is not sufficient to generate the required amount of seeds for the granulation unit.

Still referring to said third embodiment, said minor portion of urea melt can be fed to the seeding section directly or via the second evaporation unit, where it is further concentrated. A further concentration is appropriate when the urea melt, as made available by the first evaporation section, would not meet requirements of the seeding section, e.g. in terms of maximum allowable content of water. Said minor portion is preferably not greater than 20% (in weight), more preferably around 5%, for example 4 to 5% of the urea melt leaving the first evaporation section.

According to further embodiments of the invention, said seeding section is a prilling tower or comprises a prilling tower. The prills produced by the prilling tower are sent to a granulator downstream, where they are enlarged by means of the granulation process. Hence the prilling tower can be regarded as a seeder of the granulation process.

In embodiments comprising a prilling tower, a contaminated air stream containing urea dust and ammonia is drawn off the prilling tower and requires scrubbing. The contaminated air stream from the granulation unit and the contaminated air stream from the prilling tower may be scrubbed together in a common unit or separately in separate scrubbing units.

Being obtained from solidification of the urea-containing stream from the second evaporation section, the seeds are made of solid urea and some amounts of ammonium salts. Preferably the content of urea in the seeds is at least 95 wt %, the rest being ammonium salts, water and impurities. Preferably, the urea and ammonium salts together constitute more than 99% (in weight) of the seeds, preferably 99.5 to 99.9%.

Preferably, the seeds produced in a seeding unit have a characteristic size of around 1 mm, preferably in the range 1 to 1.5 mm; the seeds may have a spheroidal or ellipsoidal shape; more preferably the seeds are spheres with a diameter in the above range of 1-1.5 mm. Seeds produced in a prilling tower (prills) typically range from 1 to 2 mm of diameter.

The main advantages of the process of the invention are the following.

The second evaporation and condensation sections avoid the above mentioned drawback of contamination of the waste water of the urea synthesis process. The aqueous solution of urea and ammonium salts from the scrubbing treatment is continuously recycled back to the scrubbing unit without contamination of the waste water discharged from the first evaporation and condensation section, and is not released to atmosphere.

Additionally, the use of the urea-containing stream recovered from the second evaporation section for the production of finishing seeds acting as starting points for the granulation process helps better control the granulation itself, including formation of solid granules closer to ideal spherical shape and required size, and less dispersion of size and mass of the granules.

A further advantage of the invention is that the ammonium salts lower the urea crystallization temperature in the additional evaporation unit. Said effect is due to formation of an eutectic. Accordingly, the evaporation temperature can be lower and less biuret (which is undesired byproduct) is formed. Typically, the evaporation temperature can be reduced by around 5° C., for example from about 130-135° C. to 125-130° C.

A further advantage of the invention is given by enhanced mechanical properties of the seeds.

The invention is advantageous also for revamping of urea plants, in particular for revamping of urea plants where finishing of urea is performed in a prilling tower.

A method of revamping according to a general embodiment of the invention provides that a scrubbing section, originally designed to carry out a dust scrubbing, is modified to perform also an acid scrubbing of contaminated air drawn off a finishing section. A second evaporation section and a second condensation section are added to the plant, and a liquid output line from the modified scrubbing section, carrying an aqueous solution with urea and ammonium salts, is redirected to said newly-installed second evaporation section.

Said second evaporation section produces a liquid stream containing urea and ammonium salts and a gaseous stream comprising water vapour. Said gaseous stream is condensed and recycled to the scrubbing section. At least part of said liquid stream, containing urea and ammonium salts, is solidified to generate solid particles (seeds) which are then enlarged in a granulation process. The formation of solid particles may occur in a newly-installed seeding unit and/or in an existing prilling tower of the plant. The granulation process may be carried out in an existing granulation unit of the plant or in a new granulation unit installed during the revamping.

Two exemplary embodiments of a method of revamping according to the invention are presented below.

A first embodiment is the revamping of a urea plant where finishing is based on granulation. The plant originally comprises a scrubbing section to operate a dust scrubbing of contaminated air drawn off a granulator. The revamping includes basically:

the modification of the scrubbing section, to perform also acid scrubbing;
the installation of a second evaporation and condensation section for the treatment of the liquid effluent discharged by the modified scrubbing section, now comprising ammonium salts as a product of the acid scrubbing;

the addition of a seeding section which receives a liquid stream containing urea and ammonium salts obtained in the second evaporation section, and converts said liquid stream into said solid particles of urea which are then directed to the granulator.

In some variants, part of the urea melt originally directed to the granulator may be deviated to said seeding section, if necessary, or a portion of said liquid stream containing urea and ammonium salts may be sent directly to the granulator (bypassing the seeding section).

A second embodiment is the revamping of a urea plant where finishing is based on the prilling process. In this case, revamping of the plant may result in increased flow rate of urea melt, e.g. due to revamping of the urea synthesis and/or urea recovery section, exceeding the capacity of the existing prilling tower. The method of the invention solves also this problem.

For example the revamping comprises the following steps:
the scrubbing section is modified to perform also acid scrubbing and a second evaporation and condensation section is installed, similarly to the first embodiment mentioned above;
a granulation unit is added downstream of the existing prilling tower;
a first portion of the available urea melt is sent to the prilling tower and a second portion of the urea melt is sent to the newly installed granulation unit;
at least part of the liquid stream containing urea and ammonium salts, generated in the second evaporation section, is sent to the prilling tower.

Accordingly, the prilling tower is used to generate said solid particles in the form of urea prills, and said solid particles are sent to the newly installed granulation unit wherein they are fattened.

The prilling tower may also be revamped whenever it is possible and economically feasible, e.g. if the capacity of the prilling tower can be increased to some extent.

It can be understood that a further advantage of this embodiment is that the finishing section can process the increased amount of urea melt without a significant revamping of the prilling tower, which would be expensive. As a matter of fact, the prilling tower is now used as a "seeder" for the new granulation unit. The latter receives the extra amount of urea melt and operates as a "fattener" of the prills generated in the prilling tower.

According to still another embodiment, the revamping of a urea plant with a prilling tower may also comprise the installation of a seeding section.

The revamping of the invention includes that a scrubbing unit designed to operate a dust scrubbing is modified to operate also acid scrubbing. Acid scrubbing can be carried out in the already existing scrubbing unit, provided said unit is adapted to do so, as is typically the case. The existing scrubbing unit is normally made of stainless steel and can be used also for acid scrubbing. Accordingly, water and acid solution are fed to the same scrubbing unit, resulting in an aqueous acid solution containing urea. Otherwise, in the event that the existing scrubber is not suitable for acid scrubbing, a new scrubber may be installed.

Dust scrubbing and acid scrubbing can also be carried out in separate scrubbing units. Then, the method of the invention may comprise the addition of a further acid scrubbing unit to operate together with the existing dust scrubbing unit.

The invention will be further elucidated by the following description of preferred embodiments thereof, given by way of non-limiting examples.

DETAILED DESCRIPTION

Figure 1:
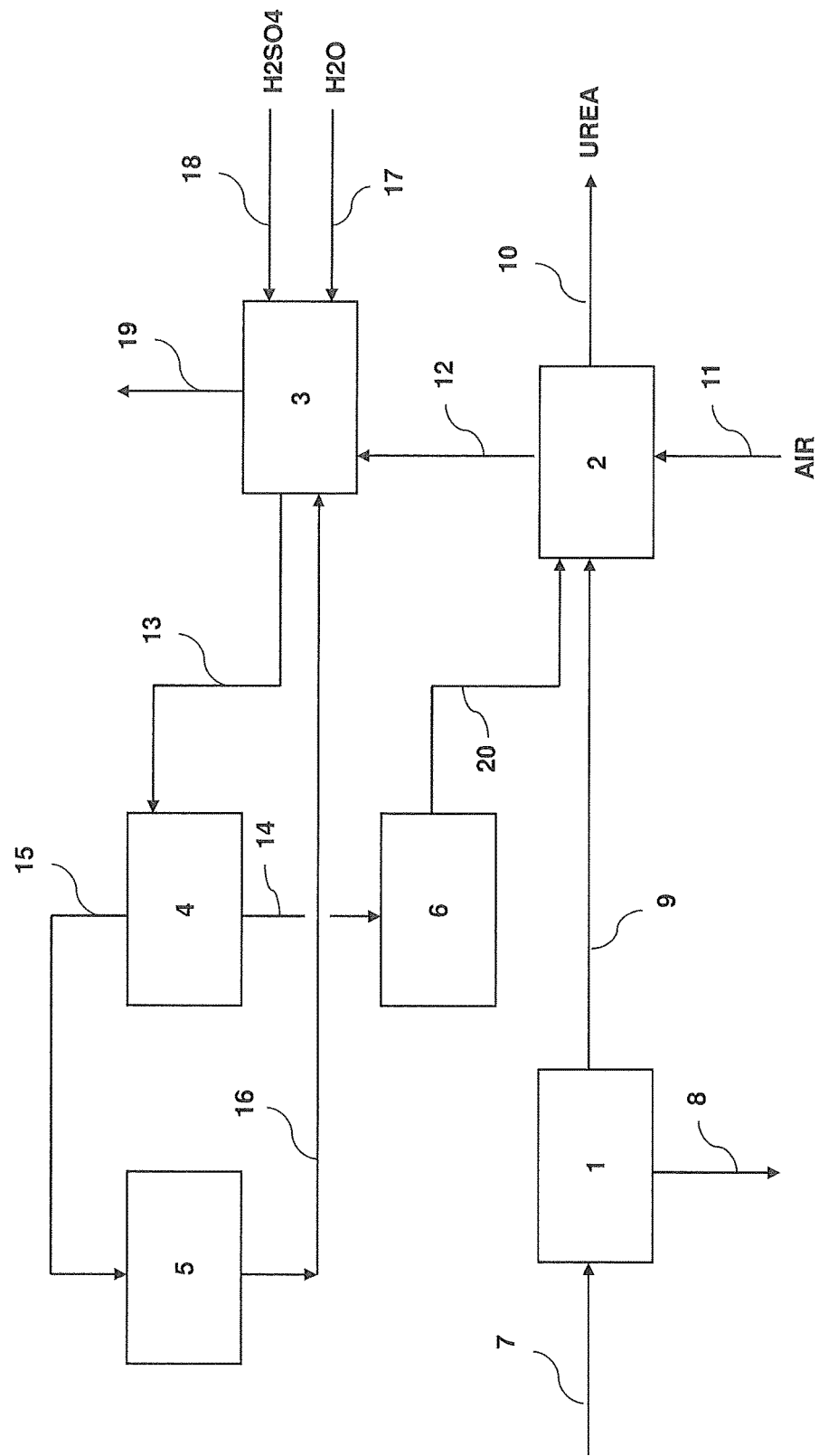
FIGS. 1-6 are schematic representations of a process for urea finishing according to different embodiments of the invention.

Referring to FIG. 1, a solution 7 resulting from the synthesis section of a urea plant (not shown) consists mainly of urea and water, and may contain small residual amounts of ammonium carbamate and ammonia. A typical concentration of this solution 7 is 60-85 wt % of urea.

Said solution 7 is fed to a first evaporation and condensation section 1, resulting in a urea melt 9 whose concentration is typically 95 to 99.9%, for example 96%. This concentration is suitable for a granulation, while a higher concentration is required for prilling. Water 8 is removed from the solution 7 and sent to a water waste treatment. Said section 1 may comprise a single stage or two stages.

The urea melt 9 is sent to a urea granulation unit 2, for example a fluid-bed granulation unit, producing solid granules of urea 10. Said granulation unit 2 is fed with a fresh air stream 11 which acts as cooling air and keeps the bed in a fluidized condition. Said air 11 then comes into direct contact with the urea melt 9 and with the solidifying urea particles inside the granulator 2. This results in a contamination of air with some urea dust and ammonia. Therefore, a stream of dust- and ammonia-laden air 12 is drawn off the granulation unit 2.

Said air 12 is treated in a scrubbing unit 3 by means of a water stream 17 to remove dust, and acid solution 18 to remove ammonia. Said solution 18 contains for example sulphuric acid. Said acid solution 18 may alternatively contain an acid selected among nitric acid, phosphoric acid, or another suitable acid.

The scrubbing in said unit 3 results in a scrubbed purified stream 19 and an aqueous solution 13 containing urea and salts formed by ammonia and the acid solution 18, for example ammonium sulphate. The content of ammonium sulphate of the solution 13 depends on the amount of ammonia in the ammonia-laden air 12 and is typically around 5%.

The stream 19 contains air which is typically saturated with water, hence a certain amount of water escapes the scrubbing unit 3 with the purified stream 19. This loss of water is compensated by the fresh water feed 17. The scrubbed air stream 19 is vented into atmosphere.

The scrubbing unit 3, in some embodiments, may comprise a separate dust scrubber fed with water 17, and an acid scrubber fed with the acid solution 18.

The solution 13 is subjected to an evaporation step in a second evaporation section 4, resulting in a gaseous stream 15 mainly consisting of water vapor, and a stream 14 containing recovered urea and the majority of ammonium sulphate of solution 13, and a small amount of water. Typically, said stream 14 contains less than 0.5% water.

The gaseous stream 15 is sent to a second condensation section 5 producing an aqueous stream 16 containing water and small amounts of urea and ammonium sulphate, which is recycled back to the scrubbing unit 3 for the scrubbing of the air 12.

The urea-containing stream 14 is fed to a dedicated seeding section 6 where it is solidified into solid particles 20 (seeds) mainly composed of urea, which are then sent to the granulation unit 2 together with the urea melt 9. In the granulation unit 2, said seeds 20 promote the granulation process acting as seeds for the growth of the granules. Preferably, the seeds 20 are spheres with a diameter of about 1-1.5 mm or less.

The seeds 20 may be produced with various techniques. For example, said seeding section 6 may comprise a rotary former depositing small droplets of urea on a cooled steel belt, or a small prilling tower. Suitable embodiments of a seeder for granulation of urea are disclosed, for example, in EP 2 077 147.

Said seeding section 6 and said granulation unit 2 form the finishing section of the urea plant.

In some embodiments, a seeding section may be installed inside a granulator.

Figure 2:
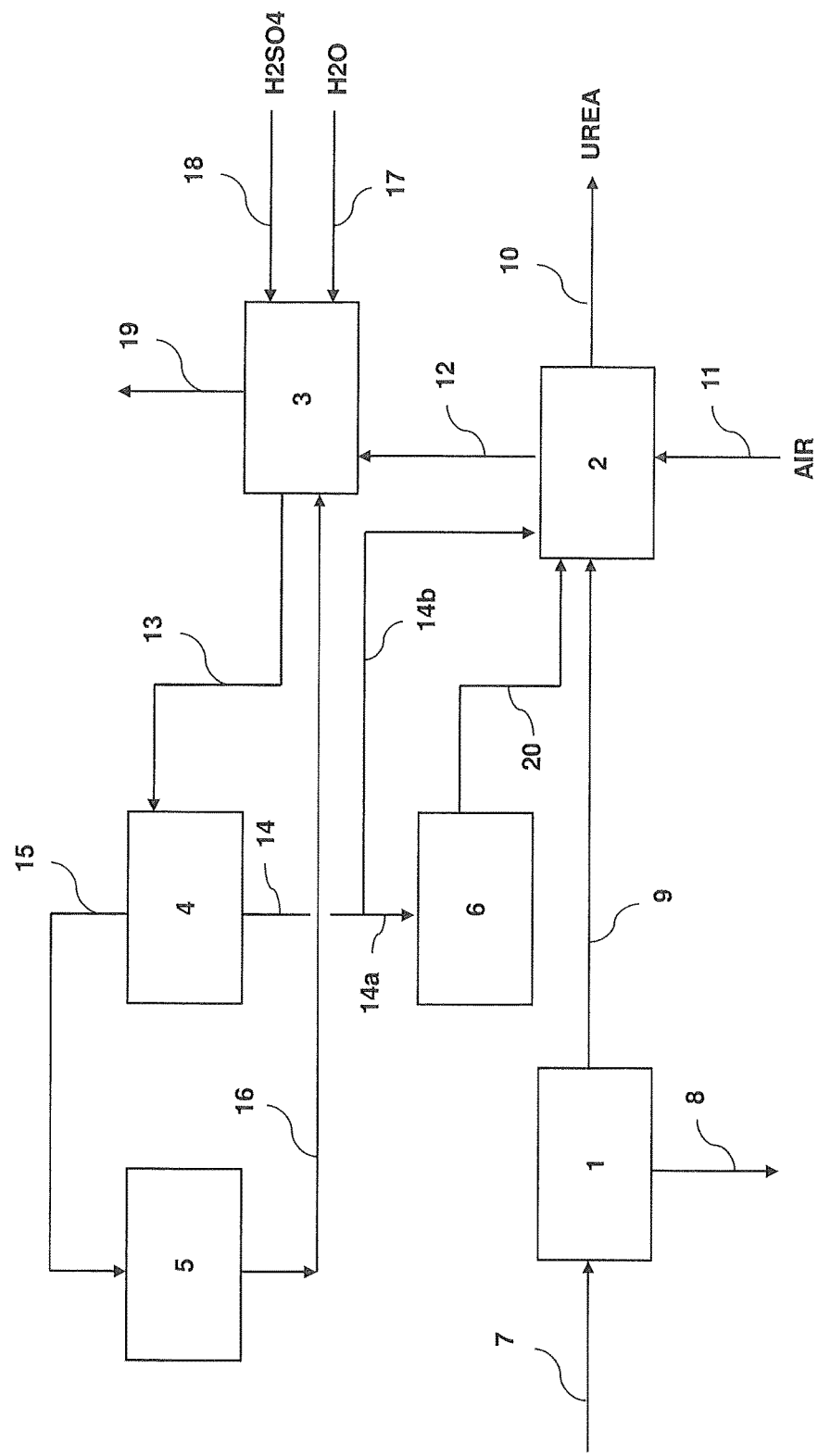

FIG. 2 shows a second embodiment of the invention which is basically a variant of FIG. 1, wherein the urea-containing stream 14 is split into a first portion 14a and a second portion 14b. The first portion 14a is sent to the seeding section 6 upstream the urea granulation unit 2; the second portion 14b is fed directly to the granulation unit 2.

Figure 3:
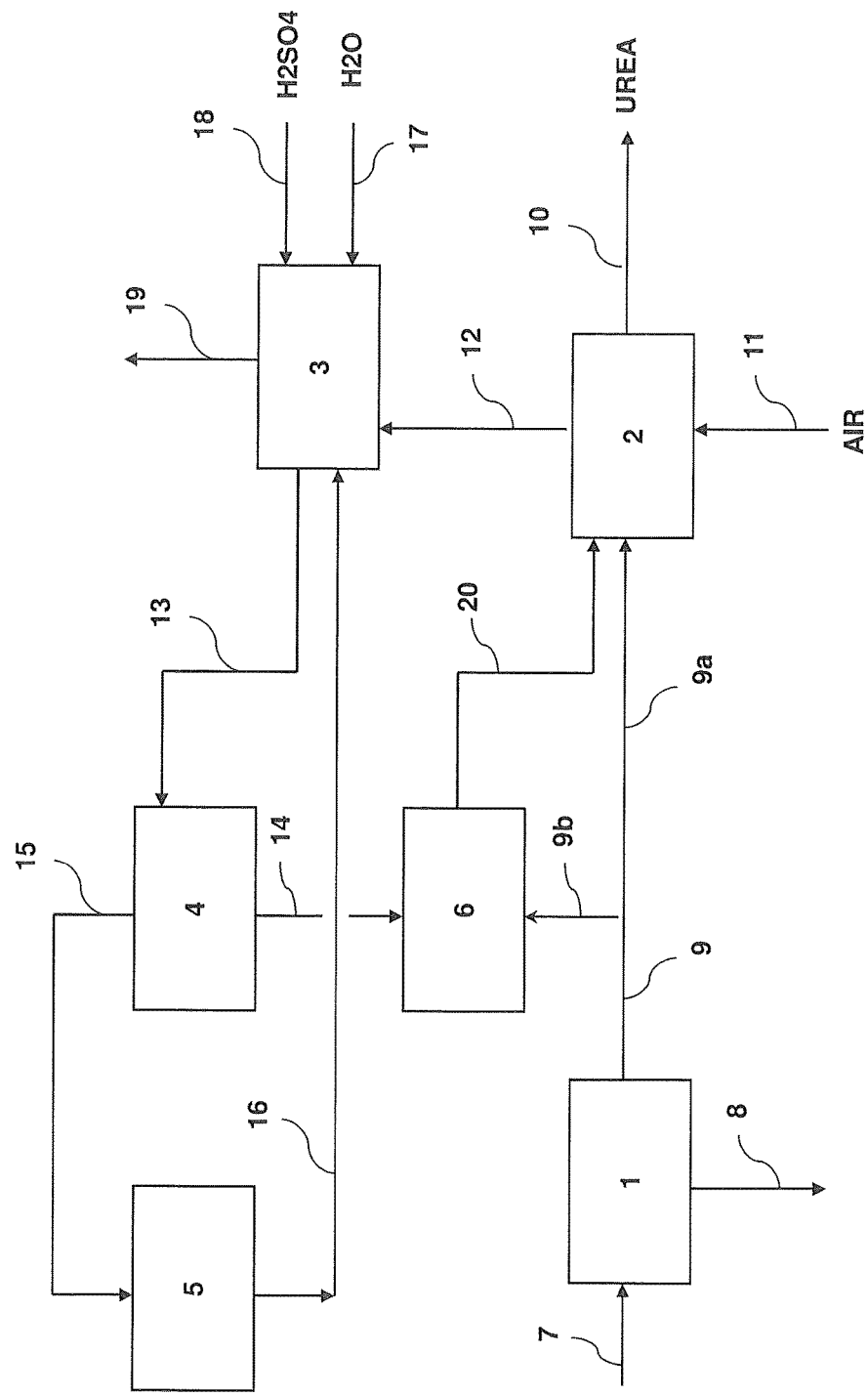
Figure 4:
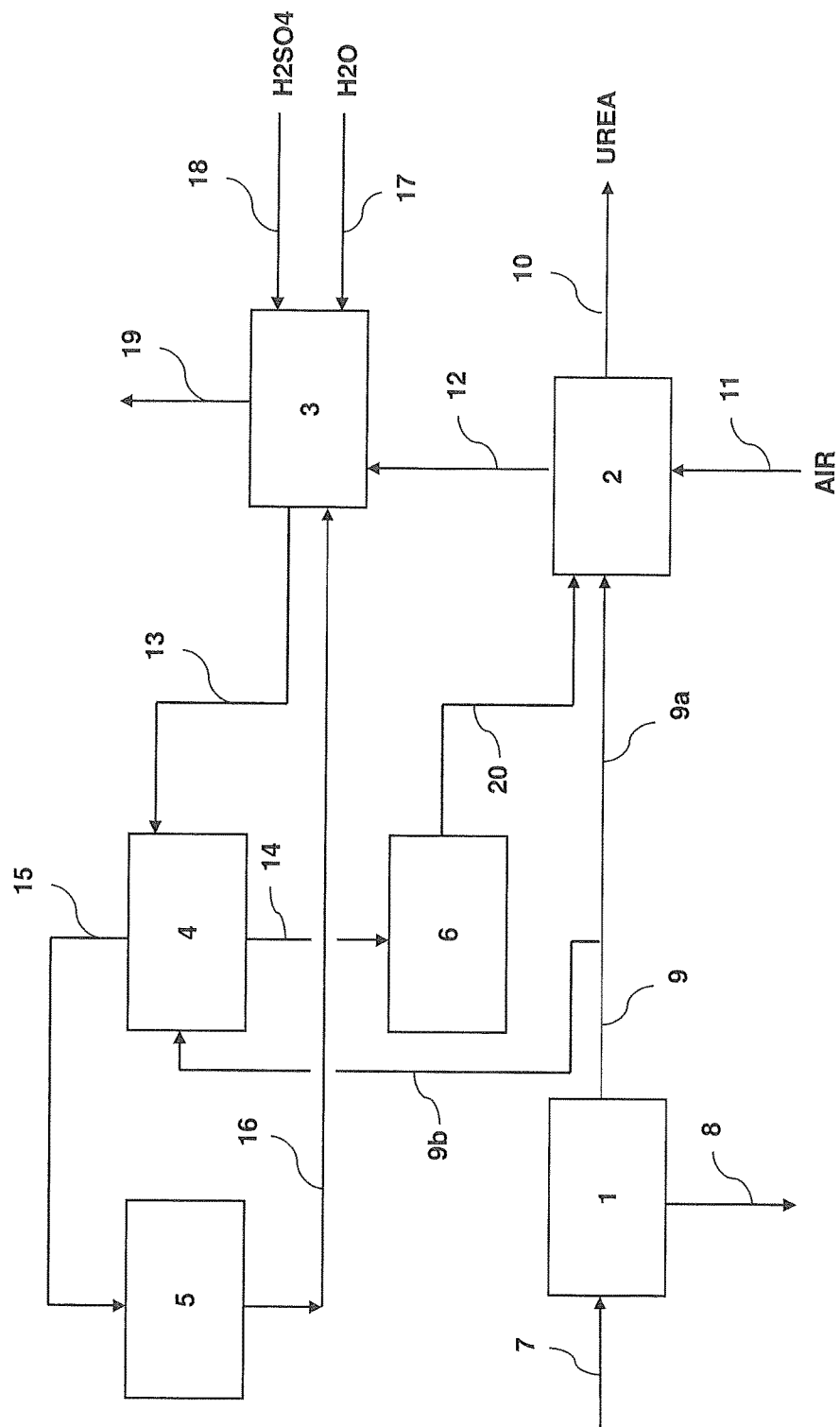

FIGS. 3 and 4 show another embodiment, wherein a portion of the urea melt 9 is used for the generation of the seeds of urea. More in detail, referring to FIG. 3, a portion 9a of the urea melt 9 is fed to the granulation unit 2 and a remaining portion 9b is sent to the seeding section 6.

Said remaining portion 9b of the urea melt feeds the seeding section 6 directly (FIG. 3) or via the second evaporator 4 where it is further concentrated (FIG. 4). Sending the urea melt directly to the seeding section 6, as in FIG. 3, is possible when the urea melt 9 has the suitable concentration. In some embodiments, the urea melt 9 may have a relatively high content of water (e.g. 4%), which is tolerated by the granulation unit 2. However such amount of water may not be tolerated by the seeding section 6, and in that case the further concentration of FIG. 4 is appropriate.

For example, the concentration of the melt 9 may vary according to the technique of finishing, for example may be 96-98 wt % (% in weight) for a granulator and typically 99.5 wt % or more for a prilling tower. The requirements of the seeding section 6 may include a maximum water content of 0.5 wt %.

Figure 5:
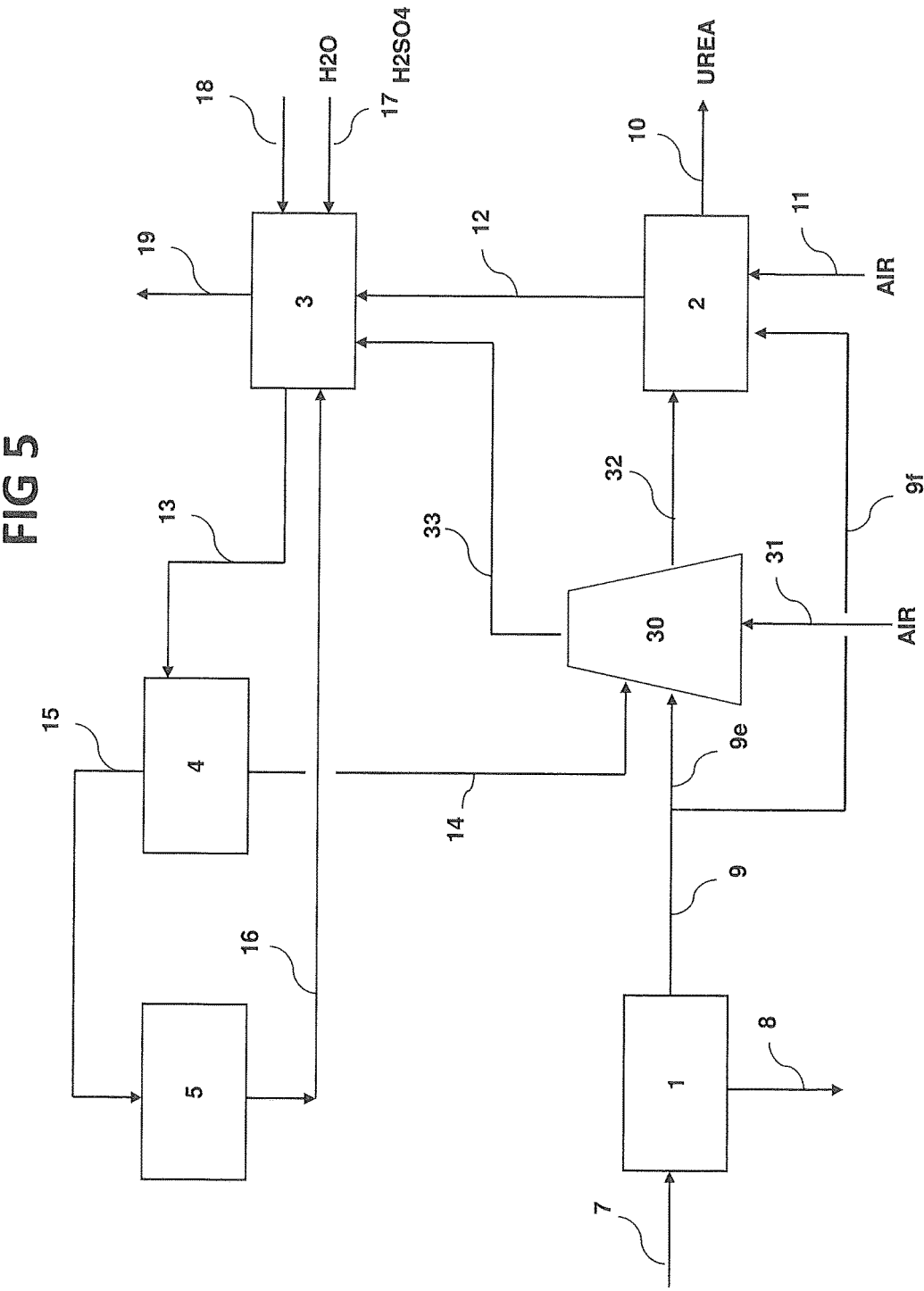

FIG. 5 shows a further embodiment of the invention including a prilling tower 30 and a granulation unit 2. Urea prills 32 produced in the tower 30 are fattened in the granulation unit 2 to form granules (fattened prills) 10.

A portion 9e of the urea melt 9 is sent to the urea prilling tower 30 and converted into liquid drops, which are solidified by counter-current air 31 rising in the tower 30. Accordingly, the tower 30 discharges a stream of dust- and ammonia-laden air 33 which need be scrubbed, similarly to the stream 12 from the granulation unit 2.

Both air streams 12 and 33 are treated in the scrubbing unit 3 and subsequently sent to the evaporation section 4, condensation section 5 and seeding section 6. The aqueous solution 14 containing urea and ammonium salts is at least partly sent to said prilling tower 30. Hence it can be said that the prilling tower 30 of FIG. 5 carries out the same role of the seeding section 6 of the previous embodiments of FIGS. 1-4, namely the production of seeds for the granulation process in the unit 2.

In some variants, the air streams 12 and 33 may be scrubbed separately. Furthermore, a portion of the solution 14 may be sent directly to the granulation unit 2.

Figure 6:
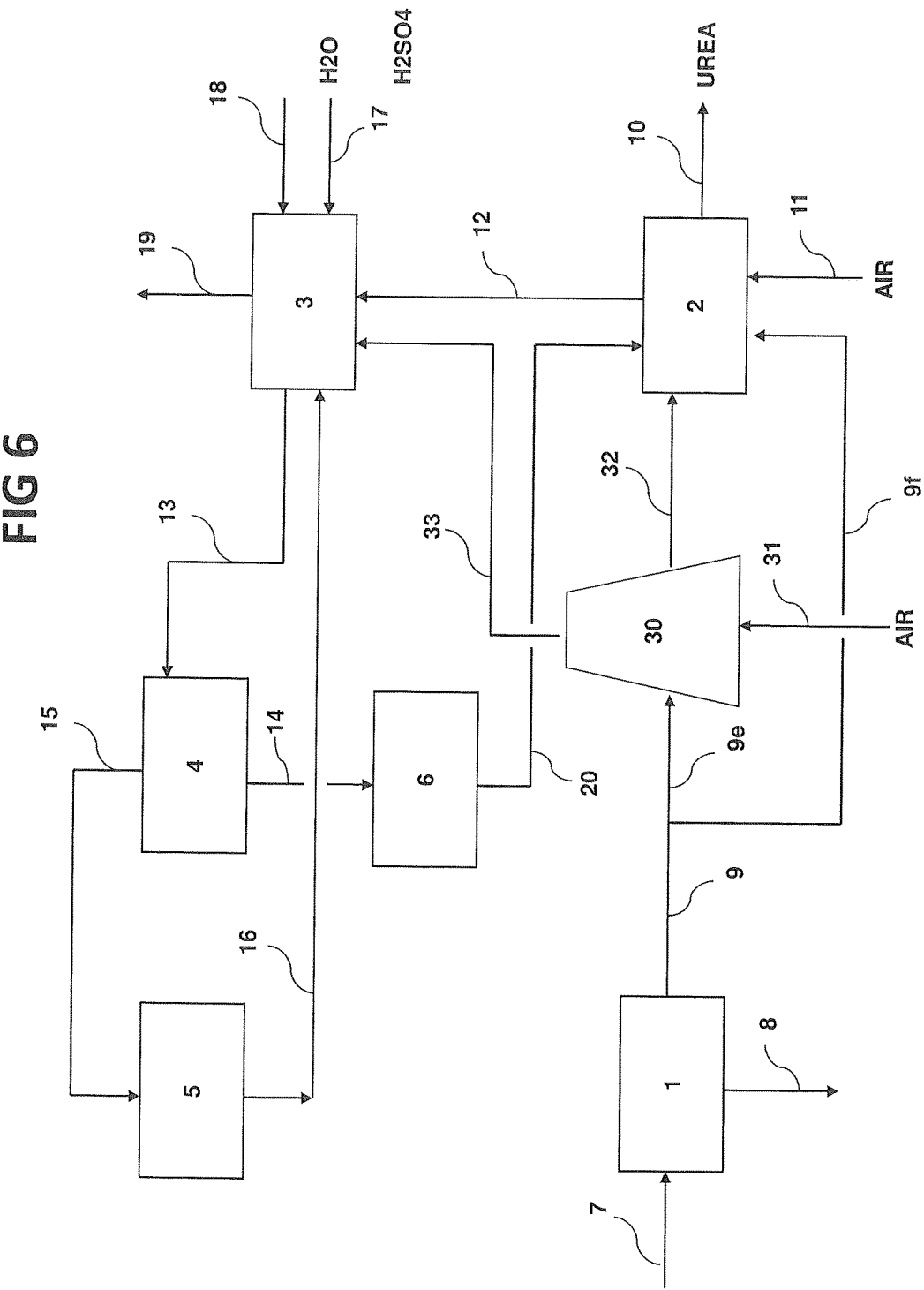

FIG. 6 shows a further variant including both a seeding section 6 and a prilling tower 30. The recovered urea 14 is fed to the seeding section 6 and converted into urea seeds 20. Urea prills 32 and urea seeds 20 are then sent to the granulation unit 2 for the growth of granules 10. Accordingly, both the solid particles 20 from the seeding section 6 and the prills 32 from the tower 30 acts as seeds for the granulation process in the unit 2.

The schemes of FIGS. 1 to 6 may be the result of a revamping process.

For example, referring to FIG. 1, a urea plant includes the first condensation and evaporation section 1, the granulator 2 and a dust scrubber. The plant is revamped by addition of second evaporation and condensation section 4, 5, the addition of the seeding unit 6, and modification of the scrubber to obtain the dust/acid scrubber 3 of FIG. 1. Then, the liquid output of the scrubber is directed to the newly installed evaporation section 4 as shown by the line 13, and the liquid stream containing urea and ammonium salts recovered by the evaporation section (line 14) is sent to the seeding section. Then the solids produced by the seeding section are sent to the granulator 2.

Similarly, a revamping may result in one of the schemes of FIGS. 2 to 4.

Referring to FIG. 5, a plant comprising a prilling tower 30 may be revamped in a similar manner, adding also a granulator 2 downstream the tower 30. In most cases, the revamping is accompanied by an increase of capacity in terms of flow rate of the urea melt 9. Accordingly, after the revamping, only a portion 9e of the urea melt is sent to the prilling tower 30, the rest being sent to the new granulator 2. The latter acts as a fattener of the prills 32. The urea-containing stream 14 is also sent to the tower 30.

FIG. 6 is a variant of the embodiment of FIG. 5 where a seeding unit 2 is also installed.

In the embodiments of FIGS. 5 and 6, the liquid stream 14 comprising urea and ammonium salts is sent entirely to the prilling tower 30 or seeding unit 6. In a variant (not shown), a portion of said stream 14 can be sent to the granulation unit 2, similarly to FIG. 2.

The invention claimed is:

1. A process for the finishing of urea comprising the steps of:
    (a) removing water from an aqueous urea solution via evaporation and condensation in a first evaporation and condensation section, obtaining a urea melt;
    (b) subjecting at least a first part of said urea melt to a finishing treatment comprising a step of granulation, said finishing treatment resulting in solid urea and contaminated air containing urea dust and ammonia;
    (c) subjecting at least part of said contaminated air to a scrubbing treatment in at least one scrubbing unit, said treatment comprising an acid scrubbing treatment with water and an acid, and a dust scrubbing, said acid scrubbing treatment producing an aqueous solution comprising urea and ammonium salts;
    (d) subjecting at least part of said aqueous solution comprising urea and ammonium salts to evaporation in a second evaporation section, obtaining a liquid stream comprising urea and ammonium salts and a gaseous stream;
    (e) subjecting said gaseous stream to condensation in a second condensation section, obtaining a recycle aqueous stream,
    (f) using at least a part of said recycle aqueous stream for the scrubbing of contaminated air of point c) above,
    (g) converting at least a portion of said liquid stream comprising urea and ammonium salts into solid particles, and
    (h) using said solid particles as seeds for said step of granulation.

2. The process according to claim 1, wherein said step of granulation is carried out in a granulation unit and the formation of said solid particles of urea is carried out in at least one of a seeding section and a prilling tower, upstream said granulation unit and separate from said granulation unit.

3. The process according to claim 2, wherein said at least part of urea melt is directly subjected to said step of granulation.

4. The process according to claim 3, wherein a first part of urea melt is sent directly to said granulation unit, and a second part of urea melt is sent to said seeding section or prilling tower.

5. The process according to claim 4, wherein said second part is not greater than 20% in weight of the urea melt.

6. The process according to claim 1, wherein formation of at least part of said solid particles of urea is carried out in a prilling tower and said contaminated air stream comprises an air stream drawn off said granulation unit and cooling air drawn off said prilling tower, the air from the granulation unit and the air from the prilling tower being scrubbed in the same scrubbing unit or in in respective and separate scrubbing units.

7. The process according to claim 1, process further comprising sending a first portion of said liquid stream comprising urea and ammonium salts to said at least one seeding section or prilling tower, and sending a second portion of said stream to said granulation unit.

8. The process according to claim 1, the process further comprising entirely sending said liquid stream comprising urea and ammonium salts to said seeding section or prilling tower.

9. The process according to claim 1, the process further comprising sending said aqueous solution comprising urea and ammonium salts directly to said second evaporation section from said scrubbing unit.

10. The process according to claim 1, wherein acid scrubbing is carried out with an acid selected in the group of sulphuric acid, nitric acid and phosphoric acid.

11. An apparatus for the finishing of urea comprising:
(a) an evaporation and condensation section removing water from an aqueous urea solution and producing a urea melt;
(b) a finishing section comprising at least a granulation unit, and optionally a prilling tower upstream said granulation unit, and converting at least a first part of said urea melt in solid urea in the presence of air, and discharging a contaminated air containing urea dust and ammonia;
(c) at least one scrubbing unit for the scrubbing of said contaminated air, producing an aqueous solution;
(d) a second evaporation section receiving said aqueous solution comprising urea and ammonium salts, and producing a liquid stream comprising urea and ammonium salts, and a gaseous stream;
(e) a second condensation section receiving said gaseous stream and producing a recycle aqueous stream recycled back to said at least one scrubbing unit;
(f) at least one seeding unit or prilling tower wherein at least a portion of said liquid stream (14) comprising urea and ammonium salts is converted into solid particles;
(g) the plant also comprising a seeding line for introducing said solid particles into said granulation unit.

12. A method for revamping a urea plant, said plant comprising:
a synthesis section and a recovery section, producing aqueous urea solution;
an evaporation and condensation section removing water from said aqueous urea solution and producing a urea melt;
a finishing section converting at least a first part of said urea melt in solid urea and releasing a stream of contaminated air containing urea dust and ammonia, said finishing section comprising a granulation unit or a prilling tower;
a scrubbing section operating a dust scrubbing of said contaminated air stream;
said method being characterized in that:
modifying said scrubbing section to perform an acid scrubbing treatment besides said dust scrubbing, thus removing ammonia from said contaminated air and producing an aqueous solution comprising urea and ammonium salts;
adding a second evaporation section and a second condensation section to said plant;
arranging a liquid output line to carry at least part of said aqueous solution with urea and ammonium salts to said second evaporation section, so that said second evaporation section produces a liquid stream containing urea and ammonium salts and a gaseous stream comprising water vapour;
wherein said second condensation section is arranged to condense said gaseous stream from the second evaporation section, obtaining an aqueous stream, and providing a flow line to recycle said aqueous stream to said scrubbing section,
whereby the plant is modified so that at least part of said liquid stream containing urea and ammonium salts is converted into solid particles, and said solid particles are directed to said granulation unit of the plant, or a new granulation unit installed downstream of said prilling tower and acting as a fattener of the solid prills produced by said prilling tower.

13. The method according to claim 12, wherein:
the plant originally comprises a granulation unit;
adding a seeding section to said plant;
conversion of said liquid stream containing urea and ammonium salts into solid particles is carried out in said seeding section.

14. The method according to claim 12, wherein:
the plant originally comprises a prilling tower;
adding a granulation unit downstream of the existing prilling tower;
conversion of said liquid stream containing urea and ammonium salts into solid particles is carried out in said prilling tower.

15. The method according to claim 14, the method further comprising:
increasing the flowrate of the urea melt by revamping the synthesis section and/or the recovery section of the urea plant;
sending a first portion of the urea melt to the prilling tower and sending a second portion to the newly installed granulation unit.

16. The method according to claim 14, the method further comprising adding a seeding section to said plant, said seeding section being arranged to receive at least part of said liquid stream containing urea and ammonium salts and to convert it into solid particles.

* * * * *